US012810550B2

(12) United States Patent
Zhang et al.

(10) Patent No.: US 12,810,550 B2
(45) Date of Patent: Nov. 24, 2026

(54) DETECTING AND REPRESENTING ANATOMICAL FEATURES OF AN ANATOMICAL STRUCTURE

(71) Applicant: Intuitive Surgical Operations, Inc., Sunnyvale, CA (US)

(72) Inventors: Hui Zhang, San Jose, CA (US); Junning Li, San Jose, CA (US); Bai Wang, Palo Alto, CA (US); Tao Zhao, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 91 days.

(21) Appl. No.: 18/773,097

(22) Filed: Jul. 15, 2024

(65) Prior Publication Data

US 2024/0371100 A1 Nov. 7, 2024

Related U.S. Application Data

(62) Division of application No. 17/617,869, filed as application No. PCT/US2020/036854 on Jun. 9, 2020, now Pat. No. 12,067,678.
(Continued)

(51) Int. Cl.

*G06T 17/20* (2006.01)
*A61B 34/10* (2016.01)
*G06T 7/00* (2017.01)

(52) U.S. Cl.

CPC .............. *G06T 17/20* (2013.01); *A61B 34/10* (2016.02); *G06T 7/0012* (2013.01);
(Continued)

(58) Field of Classification Search
None
See application file for complete search history.

(56) References Cited

U.S. PATENT DOCUMENTS 9,262,827 B2 2/2016 Brown et al.
10,542,953 B2 1/2020 Krimsky
(Continued)

FOREIGN PATENT DOCUMENTS

CN 1981717 A 6/2007
CN 105188524 A 12/2015
(Continued)

OTHER PUBLICATIONS

Gerard S.E., et al., "FissureNet: A Deep Learning Approach For Pulmonary Fissure Detection in CT Images." IEEE Transactions on Medical Imaging, Jan. 2019, vol. 38 (1), 30 pages.
(Continued)

*Primary Examiner* — Jeffrey J Chow

(57) ABSTRACT

An exemplary system accesses a three-dimensional (3D) model of an anatomical structure, applies a first detection process to the 3D model to detect a single-layer anatomical feature in the anatomical structure, applies a second detection process, different from the first detection process, to the 3D model to detect a non-single-layer anatomical feature in the anatomical structure, and provides a representation of the anatomical structure based on the 3D model, the detected single-layer anatomical structure, and the detected non-single-layer anatomical structure. In some implementations, the representation of the anatomical structure and a representation of a potential path to be traversed by a medical instrument in the anatomical structure are displayed.

20 Claims, 16 Drawing Sheets

Related U.S. Application Data

(60) Provisional application No. 62/860,196, filed on Jun. 11, 2019.

(52) U.S. Cl.
CPC ... *A61B 2034/105* (2016.02); *A61B 2034/107* (2016.02); *G06T 2207/30064* (2013.01); *G06T 2207/30101* (2013.01); *G06T 2210/41* (2013.01)

(56) References Cited

U.S. PATENT DOCUMENTS

| | | | |
|---|---|---|---|
| 2003/0053697 | A1 | 3/2003 | Aylward et al. |
| 2009/0190815 | A1 | 7/2009 | Dam et al. |
| 2011/0085720 | A1 | 4/2011 | Averbuch |
| 2011/0274327 | A1 | 11/2011 | Wehnes et al. |
| 2012/0230566 | A1 | 9/2012 | Dean et al. |
| 2012/0230572 | A1 | 9/2012 | Kohlberger et al. |
| 2014/0180063 | A1 | 6/2014 | Zhao et al. |
| 2015/0366481 | A1* | 12/2015 | Voth ....................... A61B 5/063 600/523 |
| 2016/0000356 | A1 | 1/2016 | Brown et al. |
| 2017/0224301 | A1 | 8/2017 | Radhakrishnan et al. |
| 2017/0323473 | A1 | 11/2017 | Wright et al. |
| 2019/0180442 | A1* | 6/2019 | Saha ...................... A61B 6/032 |
| 2019/0318484 | A1* | 10/2019 | Dougherty ................ G06T 7/11 |
| 2022/0039868 | A1 | 2/2022 | Chaoui et al. |
| 2022/0156942 | A1 | 5/2022 | Chaoui et al. |
| 2022/0254104 | A1 | 8/2022 | Zhang et al. |

FOREIGN PATENT DOCUMENTS

| | | | |
|---|---|---|---|
| CN | 106659373 | A | 5/2017 |
| CN | 106821498 | A | 6/2017 |
| CN | 107087856 | A | 8/2017 |
| CN | 107871531 | A | 4/2018 |
| CN | 108451639 | A | 8/2018 |
| EP | 3213296 | A1 | 9/2017 |

OTHER PUBLICATIONS

International Preliminary Report on Patentability for Application No. PCT/US2020/036854 mailed on Dec. 23, 2021, 14 pages.

International Search Report and Written Opinion for Application No. PCT/US2020/036854, mailed on Oct. 26, 2020, 19 pages.

Invitation to pay additional fee received from the International Search Authority for PCT/US2020/036854, mailed Sep. 2, 2020, 13 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Ofice Action for Chinese Application No. CN202080051727, malled Jan. 5, 2025, 40 pages.

Yuan G., "Quality Inspection of 3D Printed Medical Guide Plates Using a Combination of 3D Models and Machine Vision," China Master Thesis Database, Information Technology Collection, 2016, 77 Pages.

Zhang Q., et al., "3D Path Planning for Anterior Spinal Surgery Based on CT Images and Reinforcement Learning," 2018 IEEE International Conference on Cyborg and Bionic Systems, Oct. 2018, pp. 317-321.

Zhang X.Q., et al., "Construction of Three-dimensional Models of Cardiac Fibrous Skeleton and Valves and Application of the 3d Printed Models," Journal of Third Military Medical University, 2018, vol. 40(4), pp. 1251-1257.

* cited by examiner

DETECTING AND REPRESENTING ANATOMICAL FEATURES OF AN ANATOMICAL STRUCTURE

RELATED APPLICATIONS

The present application is a divisional of U.S. patent application Ser. No. 17/617,869, filed Dec. 9, 2021, which is a U.S. National Stage Application under 35 U.S.C. § 371 of International Application No. PCT/US2020/036854, filed Jun. 9, 2020, which claims priority to U.S. Provisional Patent Application No. 62/860,196, filed Jun. 11, 2019, each of which is hereby incorporated by reference in its entirety.

BACKGROUND INFORMATION

Pre-operative images of a patient are often used to plan a surgical procedure. Pre-operative images may include images captured using a computed tomography (CT) scan, magnetic resonance imaging (MRI), or other such imaging modalities. Such pre-operative images may be used by a surgeon, other surgical team members, and/or a procedure planning computing system to determine planned incision points, instrument paths, and other aspects of the procedure. However, identifying certain anatomical features from pre-operative images may be difficult or time-consuming.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary method includes a processor accessing a three-dimensional (3D) model of an anatomical structure of a patient, and applying a detection process to the 3D model to detect a single-layer anatomical feature in the anatomical structure, the detection process comprising generating, from the 3D model, a probability map of candidate points for the single-layer anatomical feature, generating, based on the probability map of candidate points, a single-layer mesh representing the single-layer anatomical feature.

An exemplary system includes a memory storing instructions and a processor communicatively coupled to the memory and configured to execute the instructions to access a three-dimensional (3D) model of an anatomical structure of a patient, and apply a detection process to the 3D model to detect a single-layer anatomical feature in the anatomical structure, the detection process comprising generating, from the 3D model, a probability map of candidate points for the single-layer anatomical feature, generating, based on the probability map of candidate points, a single-layer mesh representing the single-layer anatomical feature.

An exemplary non-transitory computer-readable medium stores instructions that, when executed, direct at least one processor of a computing device to access a three-dimensional (3D) model of an anatomical structure of a patient, and apply a detection process to the 3D model to detect a single-layer anatomical feature in the anatomical structure, the detection process comprising generating, from the 3D model, a probability map of candidate points for the single-layer anatomical feature, generating, based on the probability map of candidate points, a single-layer mesh representing the single-layer anatomical feature.

Another exemplary method includes a processor accessing a three-dimensional (3D) model of an anatomical structure of a patient, applying a first detection process to the 3D model to detect a first type of anatomical feature in the anatomical structure, applying a second detection process, different from the first detection process, to the 3D model to detect a second type of anatomical feature in the anatomical structure, and providing a visualization of the anatomical structure based on the 3D model, the detected first type of anatomical feature in the anatomical structure, and the detected second type of anatomical feature in the anatomical structure.

Another exemplary system includes a memory storing instructions and a processor communicatively coupled to the memory and configured to execute the instructions to access a three-dimensional (3D) model of an anatomical structure of a patient, apply a first detection process to the 3D model to detect a first type of anatomical feature in the anatomical structure, apply a second detection process, different from the first detection process, to the 3D model to detect a second type of anatomical feature in the anatomical structure, and provide a visualization of the anatomical structure based on the 3D model, the detected first type of anatomical feature in the anatomical structure, and the detected second type of anatomical feature in the anatomical structure.

Another exemplary non-transitory computer-readable medium stores instructions that, when executed, direct at least one processor of a computing device to access a three-dimensional (3D) model of an anatomical structure of a patient, apply a first detection process to the 3D model to detect a first type of anatomical feature in the anatomical structure, apply a second detection process, different from the first detection process, to the 3D model to detect a second type of anatomical feature in the anatomical structure, and provide a visualization of the anatomical structure based on the 3D model, the detected first type of anatomical feature in the anatomical structure, and the detected second type of anatomical feature in the anatomical structure.

Another exemplary method includes applying a first detection process to a set of images to generate a three-dimensional (3D) model of an anatomical structure of a patient, applying a second detection process, different from the first detection process, to the 3D model to detect a single-layer anatomical feature in the anatomical structure, and providing a visualization of the anatomical structure based on the 3D model and the detected single-layer anatomical feature in the anatomical structure.

Another exemplary system includes a memory storing instructions and a processor communicatively coupled to the memory and configured to execute the instructions to apply a first detection process to a set of images to generate a three-dimensional (3D) model of an anatomical structure of a patient, apply a second detection process, different from the first detection process, to the 3D model to detect a single-layer anatomical feature in the anatomical structure, and provide a visualization of the anatomical structure based on the 3D model and the detected single-layer anatomical feature in the anatomical structure.

Another exemplary non-transitory computer-readable medium stores instructions that, when executed, direct at least one processor of a computing device to apply a first detection process to a set of images to generate a three-dimensional (3D) model of an anatomical structure of a patient, apply a second detection process, different from the first detection process, to the 3D model to detect a single-layer anatomical feature in the anatomical structure, and provide a visualization of the anatomical structure based on the 3D model and the detected single-layer anatomical feature in the anatomical structure.

Another exemplary system includes a processor configured to access a three-dimensional (3D) model of an anatomical structure, apply a first detection process to the 3D model to detect a single-layer anatomical feature in the anatomical structure, apply a second detection process, different from the first detection process, to the 3D model to detect a non-single-layer anatomical feature in the anatomical structure, and provide a representation of the anatomical structure based on the 3D model, the detected single-layer anatomical feature, and the detected non-single-layer anatomical feature. The system further includes a display communicatively coupled to the processor and configured to display the representation of the anatomical structure and a representation of a potential path to be traversed by a surgical instrument in the anatomical structure.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
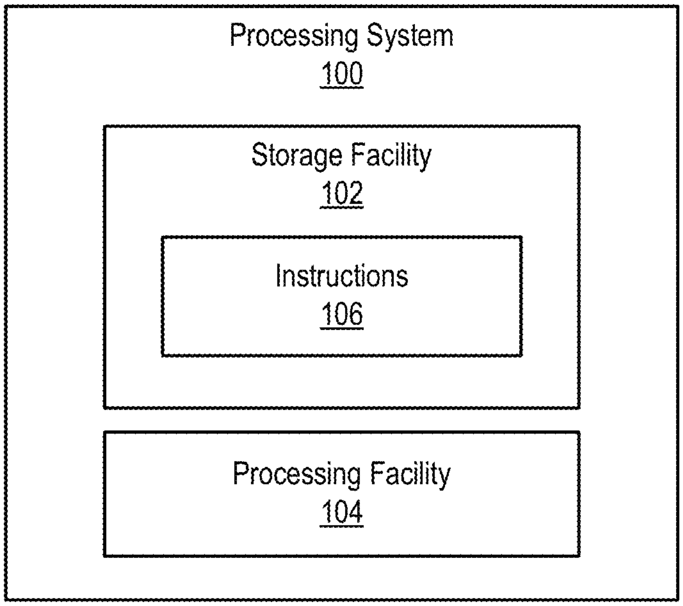
FIG. 1 illustrates an exemplary processing system according to principles described herein.

Systems and methods for detecting and representing anatomical features of an anatomical structure are described herein. In certain implementations, for example, a processing system accesses a three-dimensional (3D) model of an anatomical structure of a patient. The processing system applies a detection process to the 3D model to detect a single-layer anatomical feature in the anatomical structure. The detection process includes generating, from the 3D model, a probability map of candidate points for the single-layer anatomical feature, and generating, based on the probability map of candidate points, a single-layer mesh representing the single-layer anatomical feature.

In some examples, generating the single-layer mesh may include generating an initial single-layer mesh based on the probability map and generating a refined single-layer mesh based on the initial single-layer mesh. Generating the initial single-layer mesh may include processes such as reducing the candidate points to a subset of the candidate points, applying a signed distance transform on the subset of candidate points to generate a signed distance map, and connecting zero-crossing points in the signed distance map to form the initial single-layer mesh. Generating the refined single-layer mesh may include processes such as refining the initial single-layer mesh based on a property of the anatomical feature. For example, refining may include smoothing the initial single-layer mesh, filling holes in the initial single-layer mesh, and/or clipping the initial single-layer mesh based on the anatomical structure.

The processing system may also provide a visualization of the anatomical structure, which may include the single-layer anatomical feature, as well as one or more non-single-layer anatomical features. The processing system may use the detected anatomical features to determine or help a surgeon determine aspects of a surgical procedure.

As an example, the processing system may be used in planning an instrument path to perform a biopsy in an anatomical structure (e.g., a lung) of a patient. The processing system may access a 3D model of the lung (e.g., generate a 3D model based on pre-operative imagery, receive a 3D model, etc.). The surgeon may want to determine an instrument path that would avoid anatomical features that may be damaged by an instrument. Such anatomical features may include single-layer anatomical features (e.g., a lung fissure) as well as non-single-layer anatomical features (e.g., blood vessels, nerves, certain airways). As used herein, a single-layer anatomical feature may include any thin membrane with a same or substantially similar medium on both sides (e.g., a ligament dividing a liver into lobes, a membrane between muscle fibers, etc.). A non-single-layer anatomical feature may include any other anatomical feature. The processing system may apply detection processes to the 3D model to detect single-layer and non-single-layer anatomical features, which detection processes will be further described herein. The processing system may provide a visualization of the anatomical structure including anatomical features detected by the detection processes for use by the surgeon in planning or performing a surgical procedure. Additionally or alternatively, the processing system may use a representation of the anatomical structure including anatomical features detected by the detection processes to determine aspects (e.g., a potential instrument path) of the surgical procedure.

Methods and systems described herein for detecting and representing anatomical features of an anatomical structure may provide various advantages and benefits. For example, a single-layer mesh may provide an accurate representation of a single-layer anatomical feature, which may aid a surgeon in planning and/or performing surgical procedures. Further, detecting the single-layer feature using an automated process may save time and resources that may be allocated elsewhere to allow for more efficient and effective surgical procedures.

Various embodiments will now be described in more detail with reference to the figures. The disclosed methods and systems may provide one or more of the benefits mentioned above and/or various additional and/or alternative benefits that will be made apparent herein.

FIG. 1 illustrates an exemplary processing system 100 (also referred to herein as "system 100") configured to detect and represent anatomical features of an anatomical structure. Processing system 100 may be implemented within one or more components of a computing system and/or a computer-assisted surgical system. As shown in FIG. 1, processing system 100 includes a storage facility 102 and a processing facility 104 selectively and communicatively coupled to one another. Each of facilities 102 and 104 may include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform any of the operations described herein. For example, storage facility 102 may store instructions 106 that may be executed by processing facility 104 to perform any of the operations described herein. Instructions 106 may be implemented by any suitable application, software, code, and/or other executable data instance.

Storage facility 102 may also maintain any data received, generated, managed, used, and/or transmitted by processing facility 104. For example, as will be described below in more detail, storage facility 102 may maintain model data, image data, mesh data, surgical planning data, anatomical structure data, anatomical feature data and the like.

Processing facility 104 may be configured to perform (e.g., execute instructions 106 stored in storage facility 102 to perform) various processing operations associated with detecting and representing anatomical features of an anatomical structure in any of the ways described herein.

Figure 2:
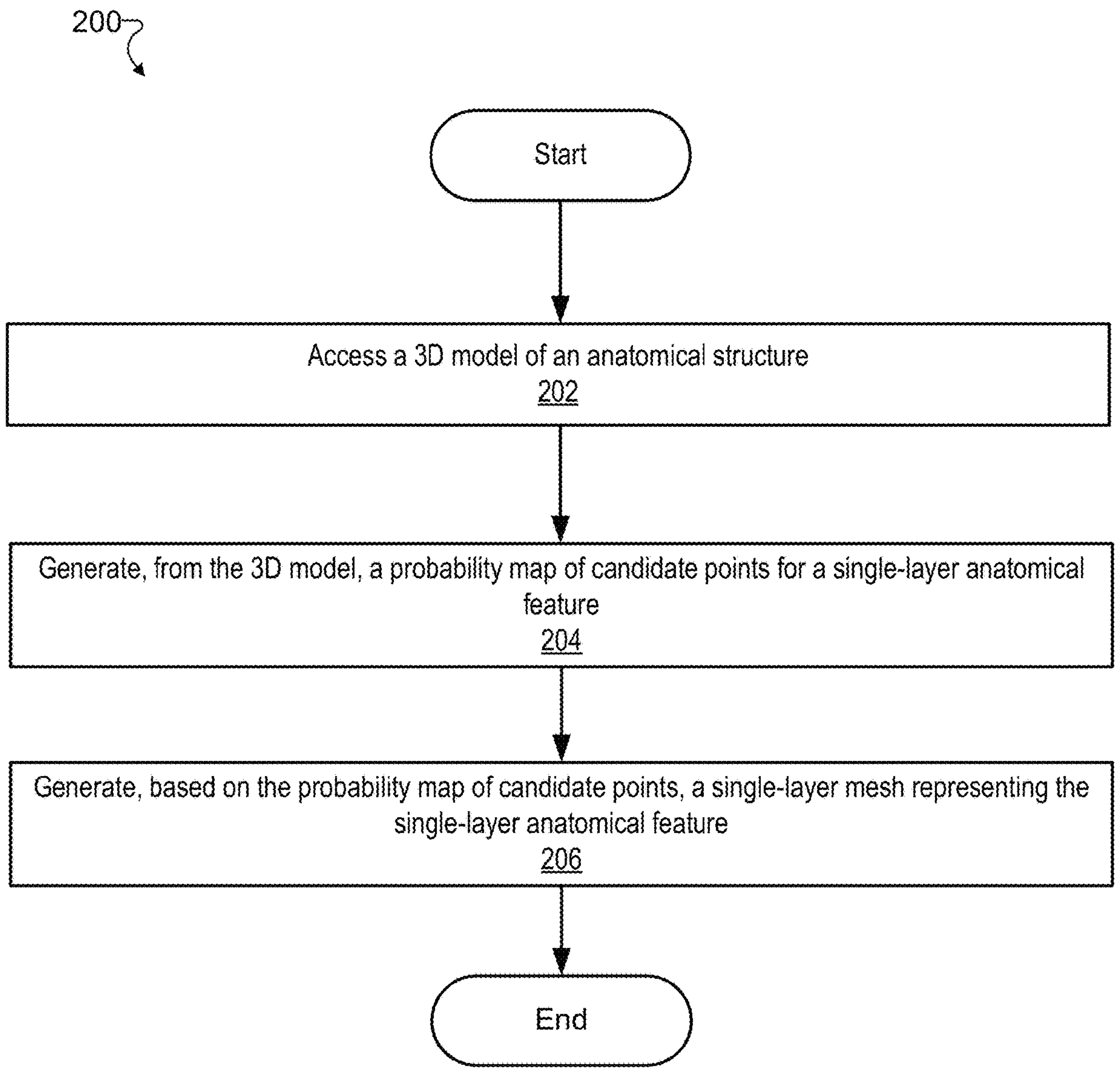
FIG. 2 illustrates an exemplary method for generating a single-layer mesh according to principles described herein.

FIG. 2 illustrates an exemplary method 200 for detecting and representing an anatomical feature of an anatomical structure. While FIG. 2 illustrates exemplary operations according to one embodiment, other embodiments may omit, add to, reorder, and/or modify any of the operations shown in FIG. 2. One or more of the operations shown in FIG. 2 may be performed by processing system 100, any components included therein, and/or any implementation thereof.

In operation 202, a processing system accesses a 3D model of an anatomical structure. In certain examples, the 3D model may be generated based on pre-operative images, such as CT scans, MRI scans, X-ray images, etc. The 3D model may be generated by processing system 100 or generated by an external system and provided to processing system 100. Exemplary ways operation 202 may be performed are described herein.

In operation 204, a processing system generates, from the 3D model, a probability map of candidate points for a single-layer anatomical feature. A candidate point may be a point for which there is a probability greater than a threshold probability that the point is a part of the single-layer anatomical feature. For example, processing system 100 may analyze the 3D model and generate a set of candidate points for which there is a probability greater than a threshold probability (e.g., 20%, 50%, etc.). The set of candidate points may constitute the probability map of the presence of a single-layer anatomical feature in the 3D model. Exemplary ways operation 204 may be performed are described herein.

In operation 206, a processing system generates, based on the probability map of candidate points, a single-layer mesh representing the single-layer anatomical feature. For example, generating a single-layer mesh may include generating an initial single-layer mesh based on the probability map and generating a refined single-layer mesh based on the initial single-layer mesh. Additionally or alternatively, generating a single-layer mesh may include reducing the candidate points to a subset of candidate points, applying a signed distance transform on the subset of candidate points to generate a signed distance map, and connecting zero-crossing points in the signed distance map to form the single-layer mesh. Exemplary ways operation 206 may be performed are describe herein.

Figure 3:
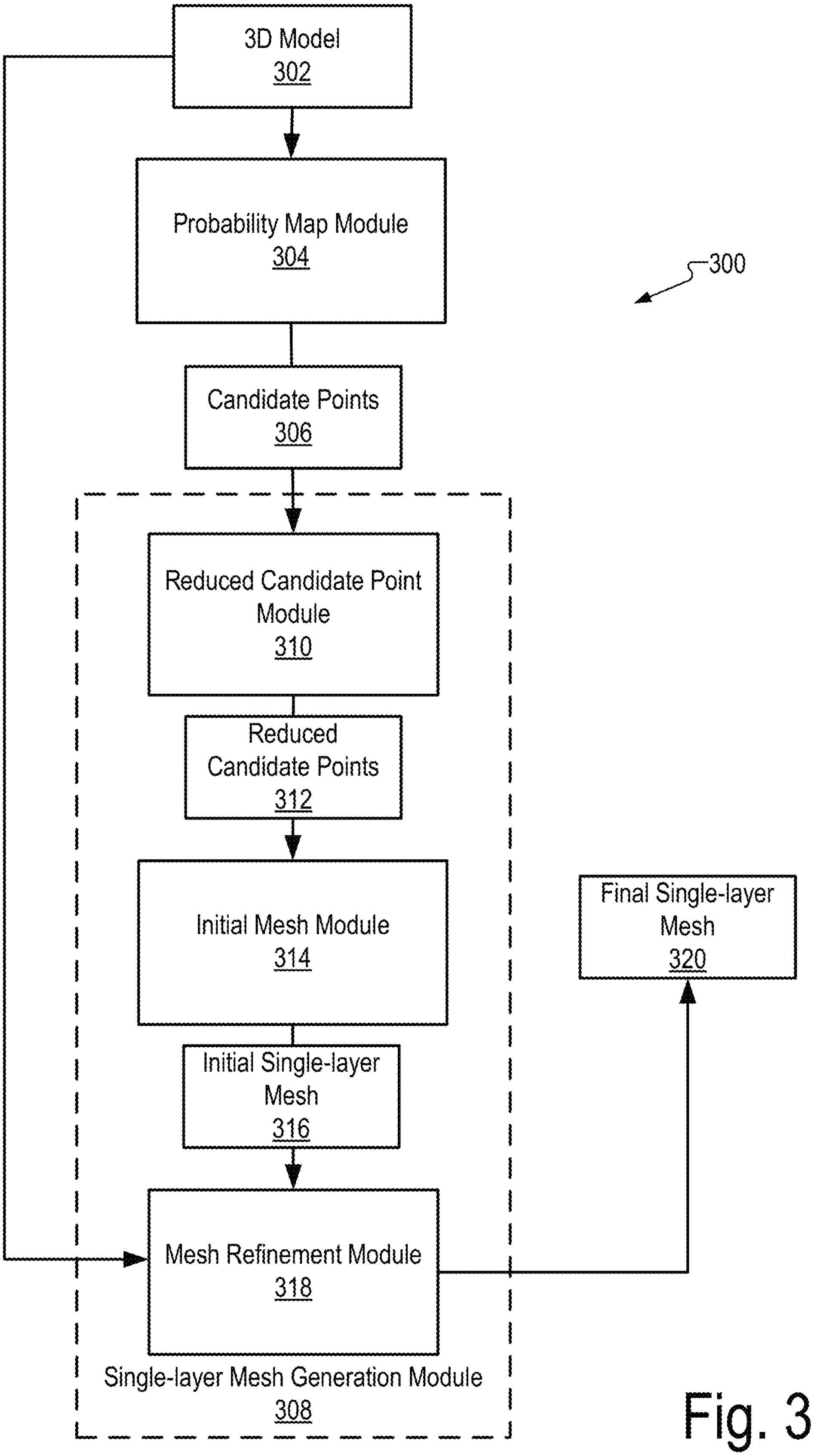
FIG. 3 illustrates an exemplary configuration for detecting a single-layer anatomical feature according to principles described herein.

FIG. 3 illustrates an exemplary configuration 300 for detecting a single-layer anatomical feature, e.g. for performing various processes or operations within methods such as method 200. Configuration 300 includes modules that access a 3D model 302 of an anatomical structure and generate a final single-layer mesh 320 representing an anatomical feature of the anatomical structure. Configuration 300 may be implemented by processing system 100 and/or any suitable components of a computer-assisted surgical system, a surgical planning system, or other computer system.

As shown, configuration 300 includes a probability map module 304, which accesses 3D model 302 of the anatomical structure. As described above, 3D model 302 may be generated by processing system 100 or generated by an external system and provided to probability map module 304.

Probability map module 304 accesses 3D model 302 of the anatomical structure and generates a set of candidate points 306. Probability map module 304 may use image processing techniques to detect, in 3D model 302, elements that indicate the single-layer anatomical feature. For each point, probability map module 304 may generate a probability (e.g., between 0 and 1) that the point is part of an element indicating the single-layer anatomical feature. The set of candidate points 306 may be the aggregation (e.g., a point cloud) of all points with probability greater than a threshold.

In certain examples, probability map module 304 may use machine learning techniques combined with image processing techniques to generate the set of candidate points 306. For example, probability map module 304 may use a convolutional neural network (CNN) approach such as U-Net, V-Net, Residual U-Net, etc., or any other suitable deep learning or machine learning technique.

Probability map module 304 provides candidate points 306 to a single-layer mesh generation module 308, which generates, based on candidate points 306, final single-layer mesh 320. As used herein, a mesh may refer to any representation of a surface and/or element (e.g., a representation of an anatomical feature) using smaller discrete shapes (e.g., polygons), which may be defined by interconnections among a set of points, 3D coordinate locations, voxels, and/or equations. A mesh may be a single-layer mesh that represents a single-layer anatomical feature, or a non-single-layer mesh that represents a non-single-layer anatomical feature or a probability map, point cloud, or another intermediate element used in generating a single-layer mesh such as final single-layer mesh 320.

As shown in FIG. 3, single-layer mesh generation module 308 includes a reduced candidate point module 310, an initial mesh module 314, and a mesh refinement module 318. Reduced candidate point module 310 receives candidate points 306 from probability map module 304 and generates, based on candidate points 306, a reduced set of candidate points (reduced candidate points 312). Reduced candidate point module 310 may reduce the set of candidate points 306 in any suitable manner. For example, reduced candidate point module 310 may use a higher threshold probability value than the threshold probability for candidate points 306 (e.g., 0.5 or 0.7 or any other suitable threshold) to generate reduced candidate points 312. Reduced candidate point module 310 may also use a threshold quantity of points (e.g., 100 or 1000 or any other suitable number of points) or a percentage of points (e.g., 50% or 25% or any other suitable percentage) to include or exclude in reducing candidate points 306 to reduced candidate points 312. Reduced candidate point module 310 may also determine an optimal threshold based on statistical analysis (e.g., Dice's coefficient, Jaccard similarity coefficient, or any other suitable similarity analysis). Reduced candidate point module 310 may also estimate initial ridge (and/or other feature) points using feature detection algorithms and techniques (e.g., Hessian matrix). Reduced candidate point module 310 may also generate reduced candidate points 312 based on any suitable combination of such thresholds.

Reduced candidate point module 310 provides reduced candidate points 312 to initial mesh module 314. Initial mesh module 314 generates, based on reduced candidate points 312, an initial single-layer mesh 316. Initial single-layer mesh 316 may include a mesh with a single-layer thickness but may also include various inaccuracies and/or uncertainties. Inaccuracies and/or uncertainties may be introduced as generation of initial single-layer mesh 316 may be based on reduced candidate points 312 (or candidate points 306) that are probabilistic. Inaccuracies and/or uncertainties may also be introduced due to artifacts and/or missing information in the 3D model and/or pre-operative imagery. Inaccuracies and/or uncertainties may also be introduced based on some of the mathematical algorithms used in generating initial single-layer mesh 316. Mesh refinement module 318 may refine initial single-layer mesh 316 to correct such inaccuracies and/or uncertainties (e.g., based on known properties of the single-layer anatomical feature, on 3D model 302, etc.) and generate final single-layer mesh 320. Initial mesh module 314 and mesh refinement module 318 may generate initial single-layer mesh 316 and final single-layer mesh 320, respectively, using any suitable techniques and algorithms. Examples of such techniques and algorithms will be further described herein.

While configuration 300 shows single-layer mesh generation module 308 including reduced candidate point module 310, initial mesh module 314, and mesh refinement module 318, in some examples single-layer mesh generation module 308 may include more modules, fewer modules, combinations of modules, etc. For instance, reduced candidate point module 310 may be optional, and initial mesh module 314 may receive candidate points 306 and generate initial single-layer mesh 316 based on a full set of candidate points 306.

Figure 4:
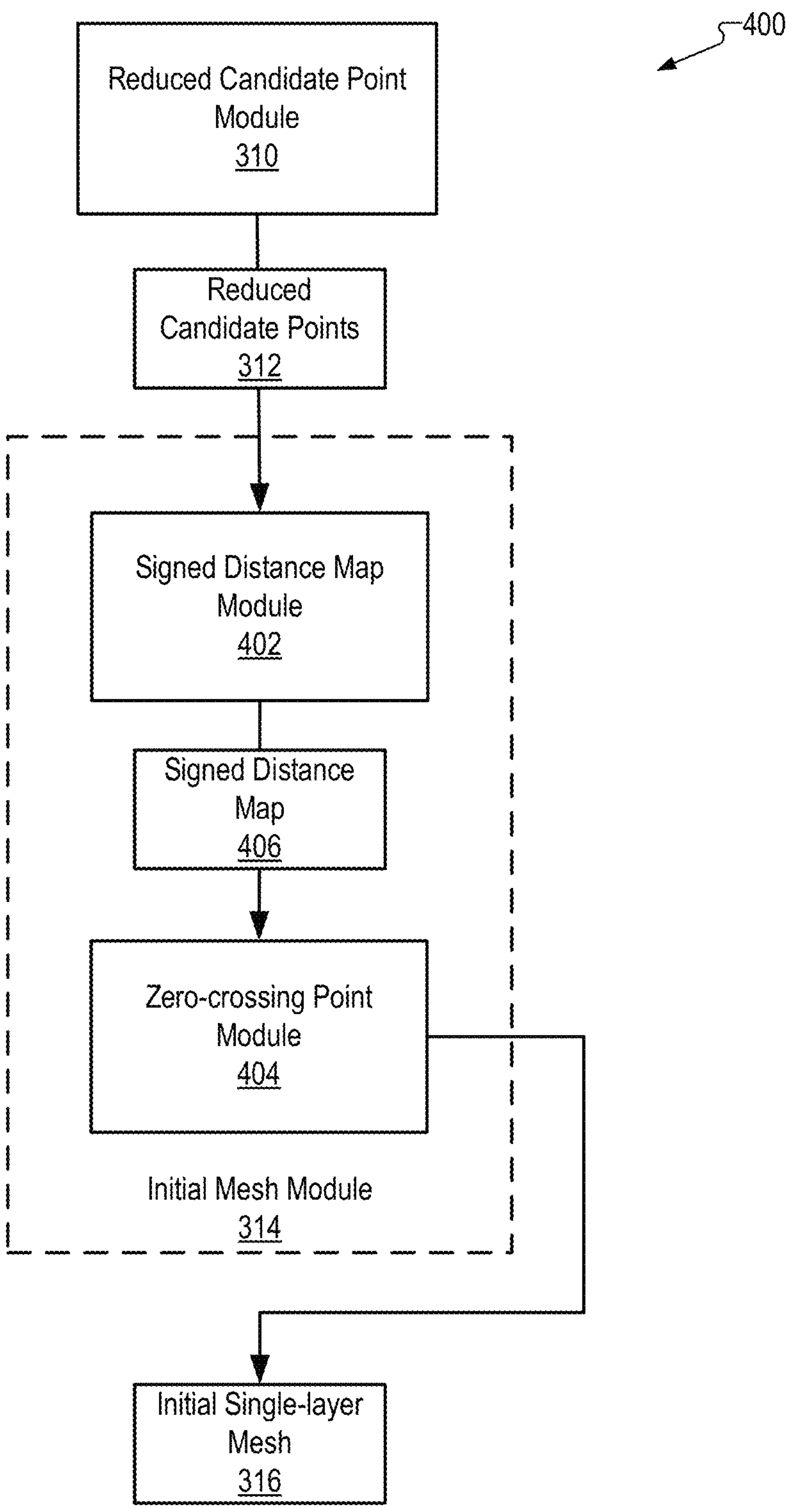
FIG. 4 illustrates an exemplary configuration for generating an initial single-layer mesh representing an anatomical feature according to principles described herein.

FIG. 4 illustrates an exemplary configuration 400 for generating an initial single-layer mesh representing an anatomical feature, e.g. for performing various processes or operations within methods such as method 200 and/or method 300, providing further details on the initial mesh module 314 of FIG. 3. Configuration 400 may be implemented by processing system 100 and/or any suitable components of a computer-assisted surgical system, a surgical planning system, or other computer system.

Similar to FIG. 3, configuration 400 shows reduced candidate point module 310, reduced candidate points 312, initial mesh module 314, and initial single-layer mesh 316. In some embodiments, the reduced candidate point module 310 may receive candidate points generated from probability map module 304 by accessing 3D model 302. Configuration 400 further shows initial mesh module 314 including a signed distance map module 402 and a zero-crossing point module 404.

Signed distance map module 402 may receive reduced candidate points 312 from reduced candidate point module 310. Signed distance map module 402 may generate, based on reduced candidate points 312, a signed distance map 406. Signed distance map module 402 may generate signed distance map 406 using any suitable techniques and algorithms. For example, signed distance map module 402 may use principal component analysis (PCA), signed distance functions, etc. to generate signed distance map 406 based on reduced candidate points 312. An example signed distance map will be described further below.

Signed distance map module 402 may provide signed distance map 406 to zero-crossing point module 404. Zero-crossing point module 404 may generate, based on signed distance map 406, initial single-layer mesh 316. Zero-crossing point module 404 may generate initial single-layer mesh 316 by analyzing signed distance map 406 to determine zero-crossing points and connecting the zero-crossing points to generate initial single-layer mesh 316. An example connection of zero-crossing points to generate an initial single-layer mesh will be described further below.

Figure 5:
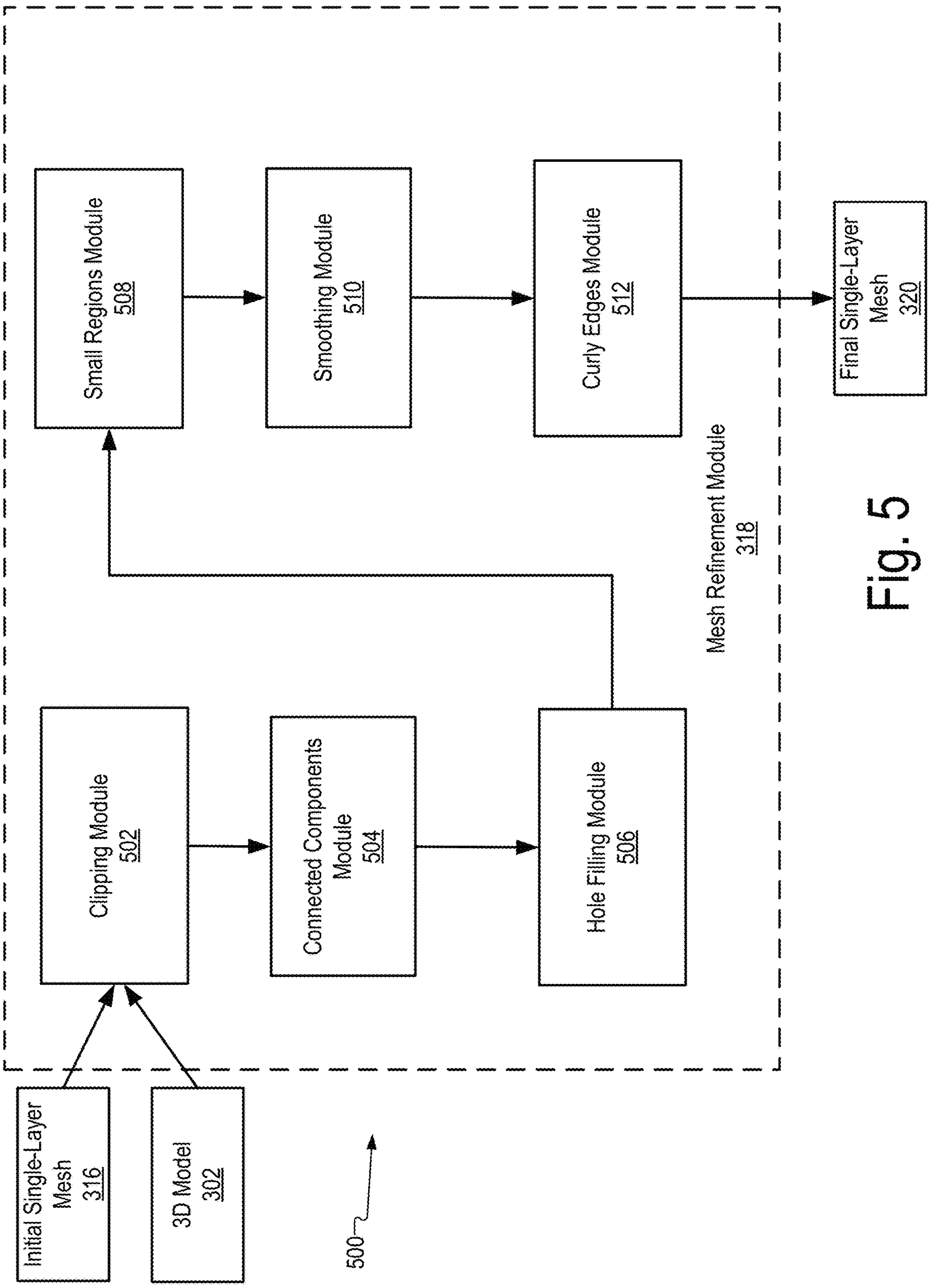
FIG. 5 illustrates an exemplary configuration for refining an initial single-layer mesh representing an anatomical feature according to principles described herein.

FIG. 5 illustrates an exemplary configuration 500 for refining an initial single-layer mesh representing an anatomical feature, e.g. for performing various processes or operations within methods such as method 200, method 300, and/or method 400, providing further details on the mesh refinement module 318 of FIG. 3. Configuration 500 may be implemented by processing system 100 and/or any suitable components of a computer-assisted surgical system, a surgical planning system, or other computer system.

Similar to FIG. 3, configuration 500 shows mesh refinement module 318 accessing initial single-layer mesh 316 and 3D model 302, and generating final single-layer mesh 320. In some embodiments the initial single-layer mesh 316 may be generated using configurations, such as configuration 400. Configuration 500 further shows mesh refinement module 318 including a clipping module 502, a connected components module 504, a hole filling module 506, a small regions module 508, a smoothing module 510, and a curly edges module 512. Such modules may be exemplary modules for refining an initial single-layer mesh based on one or more properties of the anatomical feature and/or the anatomical structure. As one example, it may be known that the anatomical feature is contained wholly within the anatomical structure. Thus, the boundaries of the anatomical feature may be constrained by the shape of the anatomical feature, and the initial single-layer mesh may be refined to conform to such constraints. Other such suitable properties of the anatomical feature and/or anatomical structure may be used to refine the initial single-layer mesh.

For example, clipping module 502 may receive initial single-layer mesh 316 and 3D model 302. Clipping module 502 may refine initial single-layer mesh 316 based on a property of the anatomical feature that the anatomical feature is contained within the anatomical structure. Thus, clipping module 502 may use 3D model 302 to clip portions of initial single-layer mesh 316 that extend outside the boundary of the anatomical structure, as provided by 3D model 302. Additionally or alternatively, clipping module 502 may extend portions of initial single-layer mesh 316 to align more closely to the boundary of the anatomical structure.

Connected components module 504 may refine initial single-layer mesh 316 based on a contiguousness of the anatomical feature. Based on such a property of the anatomical feature, connected components module 504 may combine portions of initial single-layer mesh 316 that are initially unconnected to each other. Additionally or alternatively, connected components module 504 may separate portions of initial single-layer mesh that are initially sparsely connected to each other.

Hole filling module 506 may refine initial single-layer mesh 316 based on a continuity of the anatomical feature. Based on such a property of the anatomical feature, hole filling module 506 may search for holes in initial single-layer mesh 316 and interpolate initial single-layer mesh 316 to fill such holes. Additionally or alternatively, hole filling module 506 may not fill the large holes if such holes are expected in the anatomical feature.

Small regions module 508 may refine initial single-layer mesh 316 based on a typical size of the anatomical feature. Based on such a property of the anatomical feature, small regions module 508 may detect portions of initial single-layer mesh 316 that seem too small and/or remote from a main portion of initial single-layer mesh 316 to be part of the anatomical feature. Based on such a property of the anatomical feature, small regions module 508 may determine that such small, remote portions are false positives and remove such portions from initial single-layer mesh 316.

Smoothing module 510 may refine initial single-layer mesh 316 based on a typical evenness of a surface and/or edge of the anatomical feature. Based on such a property of the anatomical feature, smoothing module 510 may modify surfaces and/or edges, such as by smoothing, roughing, patterning, or otherwise altering the surfaces and/or edges of initial single-layer mesh 316.

Curly edges module 512 may refine initial single-layer mesh 316 based on a typical structure of the anatomical feature. Based on such a property of the anatomical feature, curly edges module 512 may remove or interpolate portions of initial single-layer mesh 316. An example of such a process will be described further herein.

While FIG. 5 shows mesh refinement module 318 including each of modules 502-512, other examples or implementations of mesh refinement module 318 may include additional modules (e.g., based on other properties of the anatomical feature), fewer modules, combinations of modules, etc. While FIG. 5 shows a flow from one module to the next, in some examples, a different order of the modules may be implemented. Based on some or all of such refinements, mesh refinement module 318 may generate final single-layer mesh 320 from initial single-layer mesh 316.

Figure 6:
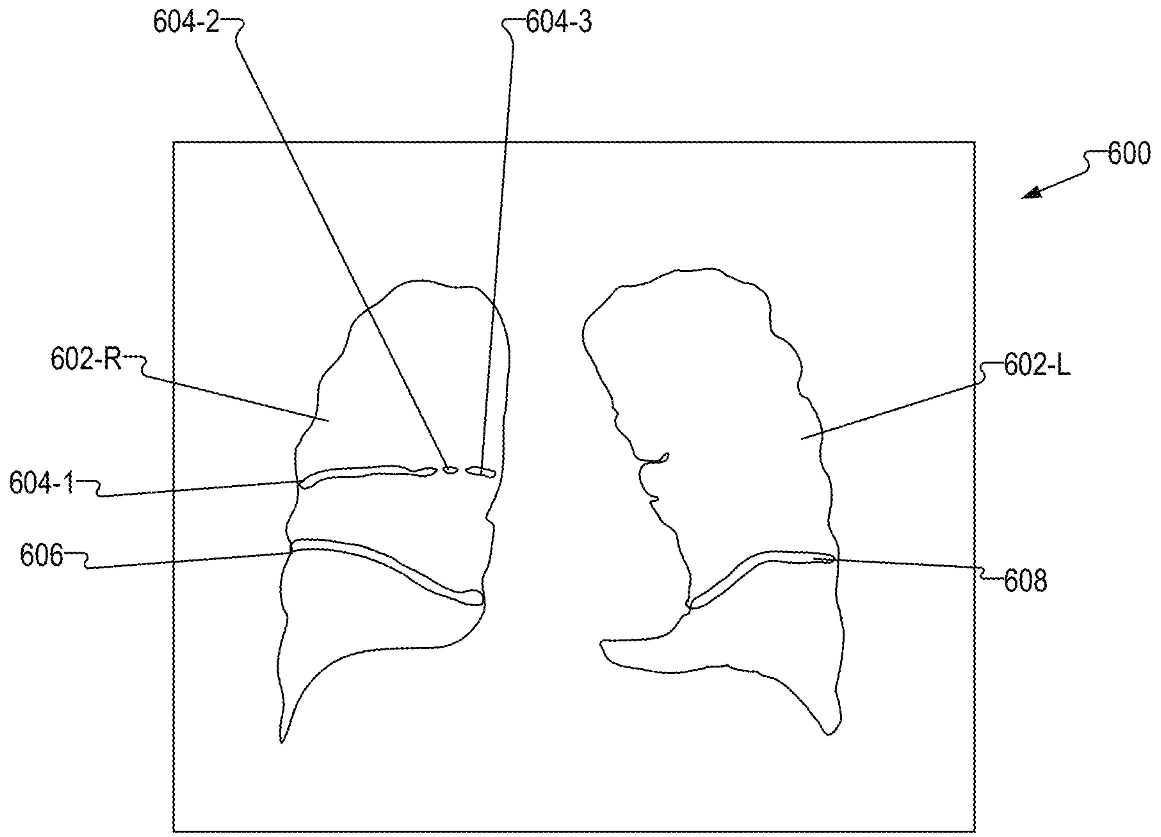
FIG. 6 illustrates an exemplary probability map for generating a single-layer mesh according to principles described herein.

FIGS. 6-12 illustrate an example application of the methods and systems described herein. The example illustrates detecting and representing lung fissures in lungs of a patient. FIG. 6 shows an image slice 600 with exemplary probability maps for generating single-layer meshes. Image slice 600 shows a two-dimensional (2D) slice of a 3D model of a pair of lungs 602 (shown as right lung 602-R and left lung 602-L) of a patient. Right lung 602-R has two fissures, dividing right lung 602-R into three lobes. Left lung 602-L has one fissure, dividing left lung 602-L into two lobes.

Image slice 600 shows right lung 602-R with a first probability map 604 (shown as three separate segments 604-1, 604-2, and 604-3) and a second probability map 606. Left lung 602-L is shown with a third probability map 608. Each of probability maps 604, 606, 608 may be an implementation of a representation of candidate points 306 or a representation of reduced candidate points 312. Image slice 600 shows each of probability maps 604, 606, 608 as a band for each of the fissures. While image slice 600 shows bands for probability maps 604, 606, 608, the bands may represent simplified visualizations of mesh structures (e.g., non-single layer meshes that may be referred to as "tongue meshes"). In other examples, any other suitable representation may be used for probability maps 604, 606, 608 such as a point cloud of candidate points, a connected mesh of candidate points or any other mesh-based representation of candidate points, a voxel-based representation of candidate points, etc.

As mentioned, each probability map 604, 606, 608 may represent a set of candidate points 306 or a reduced set of candidate points 312 for each fissure. For example, third probability map 608 may represent an aggregation of points for which a probability of each point being a part of the left lung fissure is greater than a threshold. The probability of each point may be determined using image processing and machine learning techniques as described herein. Alternatively, third probability map 608 may represent a reduced set of candidate points 312 for the presence of the lung fissure. Candidate points 306 may be reduced to generate reduced candidate points 312 in any of the ways described herein.

As shown, first probability map 604 includes three separate segments 604-1, 604-2, 604-3. The segmentation of first probability map 604 may show an example that may lead to an inaccuracy in an initial single-layer mesh generated based on first probability map 604. The segmentation may be uncertain as lung fissures are generally contiguous and continuous. Such an inaccuracy may be corrected by a mesh refinement module as described herein.

System 100 may generate single-layer meshes representative of lung fissures based on probability maps 604, 606, and 608 in any of the ways described herein. For example, based on a probability map 604, 606, or 608, system 100 may apply a signed distance transform to generate a signed distance map and, from the signed distance map, generate an initial single-layer mesh representing a fissure. System 100 may refine the initial single-layer mesh to generate a final single-layer mesh representing the fissure. Examples of such operations will now be described in more detail.

Figure 7:
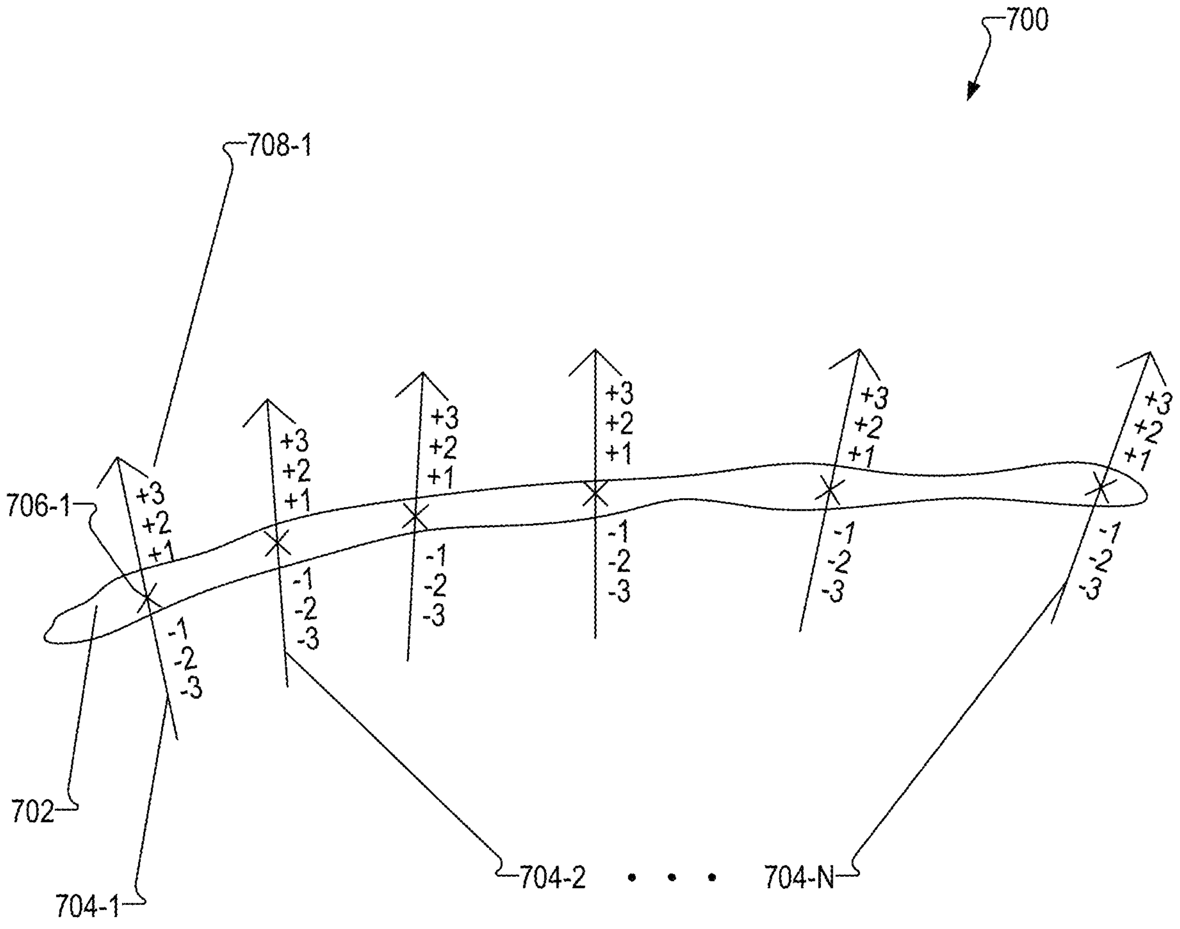
FIG. 7 illustrates an exemplary signed distance map for generating a single-layer mesh according to principles described herein.

FIG. 7 illustrates an exemplary signed distance map 700 that may be generated by system 100 and used by system 100 to generate a single-layer mesh. Signed distance map 700 may be an implementation of signed distance map 406. Signed distance map 700 shows a tongue mesh 702 (such as third probability map 608) representing a set (or reduced set) of candidate points of a lung fissure. Signed distance map 700 also includes vectors 704 (shown as vector 704-1, 704-2 . . . 704-N). Using vector 704-1 as an example, each vector 704, such as vector 704-1, shows a point 706-1, represented by an X, through which vector 704-1 passes orthogonally through tongue mesh 702. The orthogonality of vector 704-1 through tongue mesh 702 may be determined in any suitable way, such as using Hessian matrices to estimate and/or calculate normal information for points on tongue mesh 702.

Vector 704-1 further shows distance information 708-1 for points on vector 704-1. Distance information 708-1 is represented in signed numbers (e.g., +3, +2, +1, −1, −2, −3, etc.). The signed numbers may indicate both a magnitude of distance from point 706-1, as well as a direction relative to tongue mesh 702, with positive on one side of tongue mesh 702 and negative on the other side of tongue mesh 702. Signed distance map 700 may be analyzed by system 100 to determine zero-point crossings to generate an initial single-layer mesh, as described herein.

Figure 8:
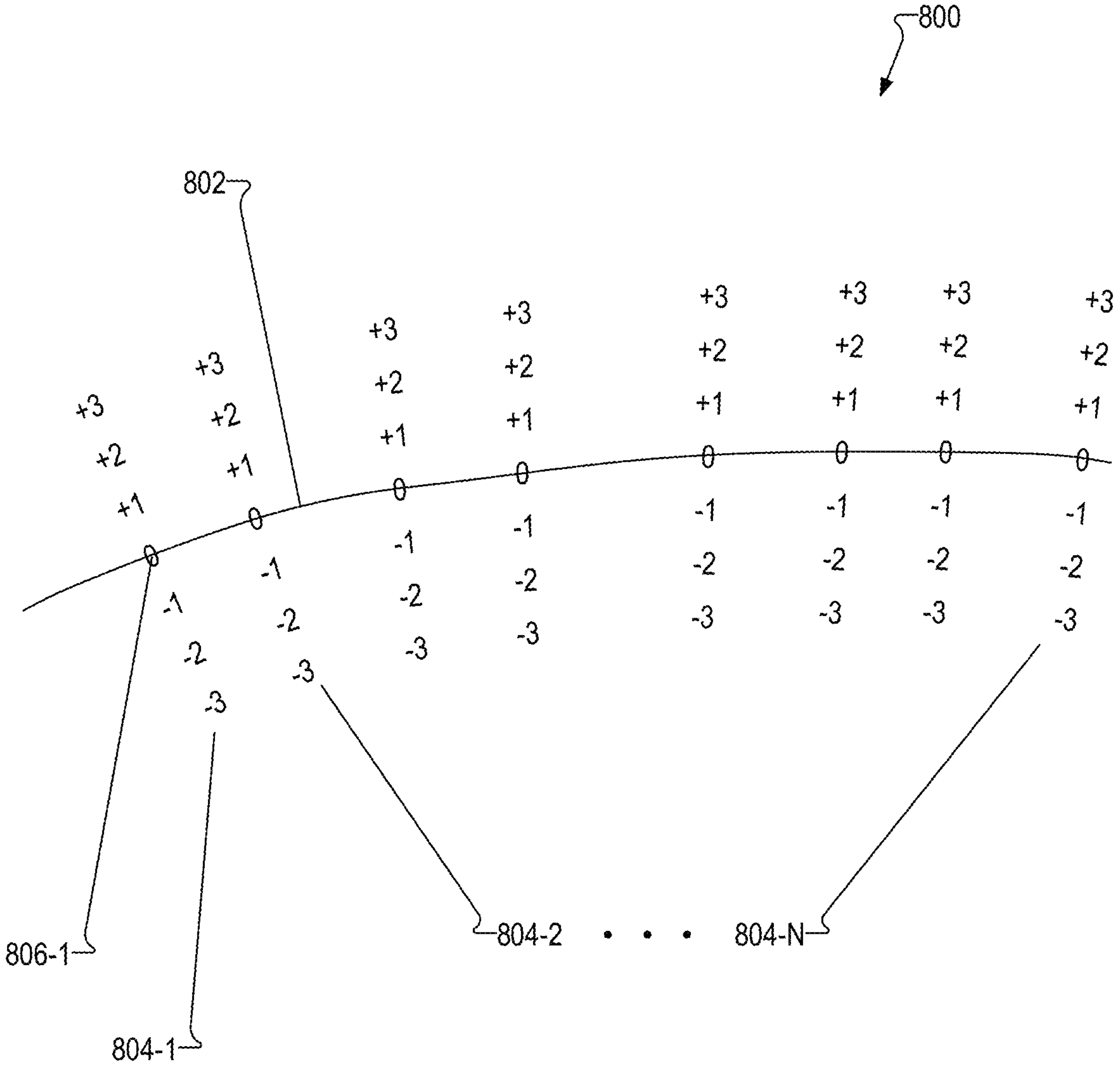
FIG. 8 illustrates an exemplary zero-crossing map for generating a single-layer mesh according to principles described herein.

FIG. 8 illustrates an exemplary zero-crossing map 800 that may be generated by system 100 and used by system 100 to generate an initial single-layer mesh 802. Zero-crossing map 800 shows number columns 804 (shown as number column 804-1, 804-2 . . . 804-N), which are generated from signed distance map 700. Using number column 804-1 as an example, each number column 804, such as number column 804-1, includes a zero 806-1, where numbers in number column 804-1 crosses from positive numbers to negative numbers (or vice versa). Connecting the zero crossing points (e.g., 806-1 and other zero crossing points) may generate a surface mesh, which may be provided as initial single-layer mesh 802.

Figure 9:
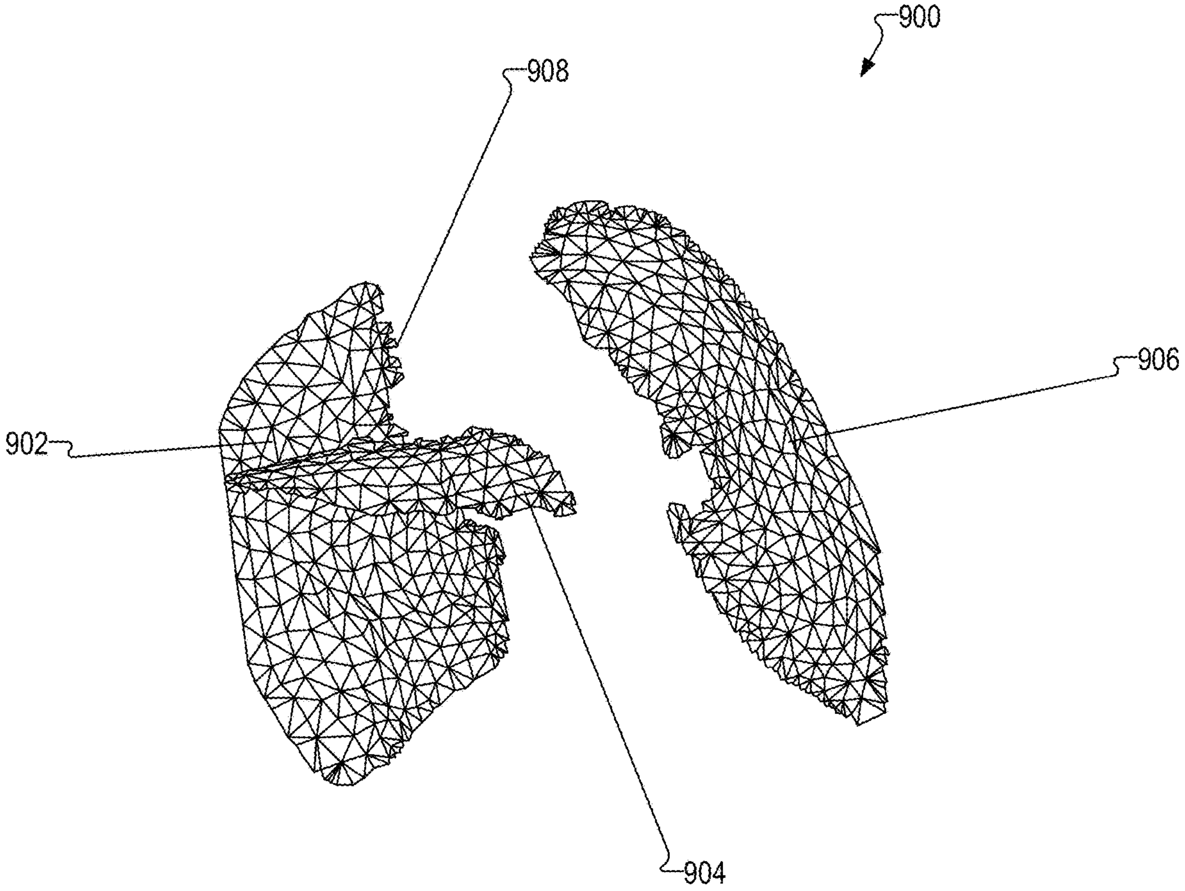
FIG. 9 illustrates an exemplary initial single-layer mesh according to principles described herein.

FIG. 9 illustrates exemplary initial single-layer meshes that may be generated by system 100 and used by system 100 to generate final single-layer meshes. FIG. 9 shows a first initial single-layer mesh 902 and a second initial single-layer mesh 904 representing two fissures of a right lung, and a third initial single-layer mesh 906 representing a fissure of a left lung. The representations of initial single-layer meshes 902, 904, 906 may be generated by system 100 in any suitable manner, such as by using a marching cubes algorithm or any other suitable computer graphics algorithm or technique to generate a mesh from information such as zero-crossing map 800.

In some examples, initial single-layer meshes 902, 904, 906 may include various inaccuracies that may be refined by a mesh refinement module. For example, first initial single-layer mesh 902 shows a jagged edge 908 that may be an uncertain representation of a typical edge of a lung fissure. To refine jagged edge 908, a smoothing module may use any suitable algorithm or technique to smooth jagged edge 908. For example, the smoothing module may average, interpolate, etc. points on jagged edge 908 to generate a smoother edge that may be a more accurate representation of the lung fissure. Additionally or alternatively, a clipping module may use a boundary of the right lung to clip or align jagged edge 908, which may also be a more accurate representation of the lung fissure as portions of lung fissures may typically be attached to inner surfaces of the lungs. Other such inaccuracies may be refined by the mesh refinement module, as described herein.

Figure 10:
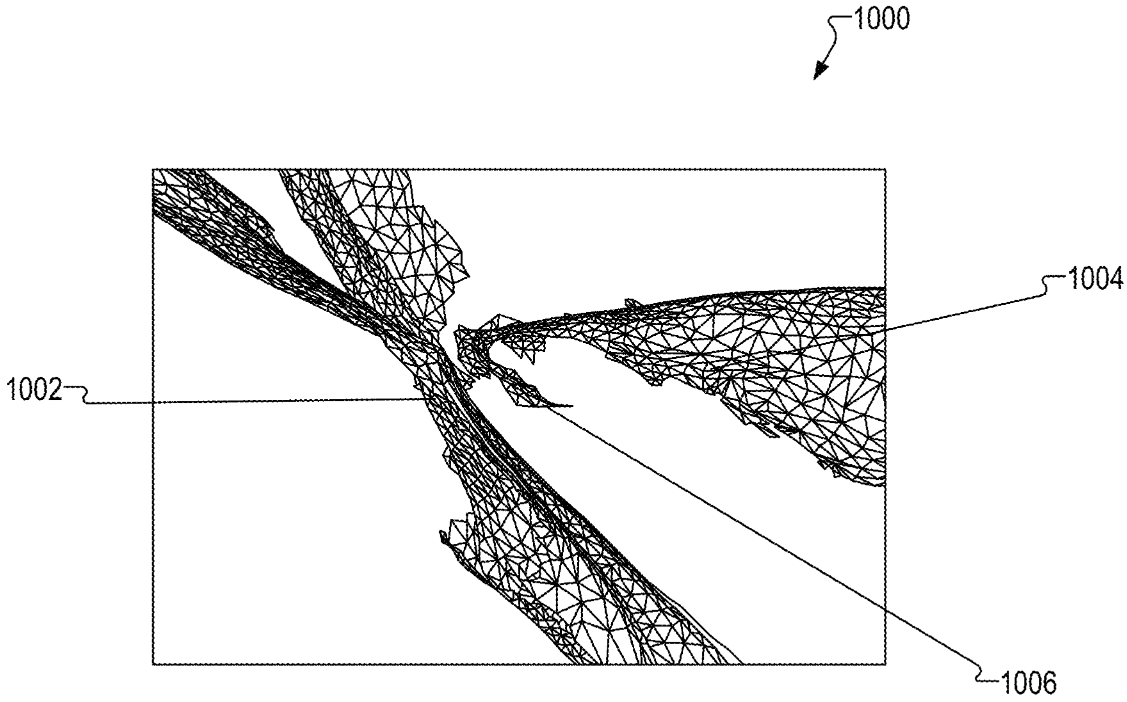
FIG. 10 illustrates an exemplary refining process for generating a single-layer mesh according to principles described herein.

FIG. 10 illustrates an exemplary refining process for generating a single-layer mesh. FIG. 10 shows two exemplary initial single-layer meshes, a first initial single-layer mesh 1002 and a second initial single-layer mesh 1004 representing two fissures of a right lung. Similar to initial single-layer meshes 902 and 904, initial single-layer meshes 1002 and 1004 may be generated by system 100 in any suitable manner, such as by using a marching cubes algorithm or any other suitable computer graphics algorithm or technique to generate a mesh from information such as zero-crossing map 800.

Second initial single-layer mesh 1004 shows an example inaccuracy of a curly edge 1006. Curly edge 1006 may be an inaccurate representation of the fissure, as fissures may typically not have such edges. Inaccuracies such as curly edge 1006 may be generated as a byproduct of an algorithm used to generate initial single-layer meshes. For example, curly edge 1006 may be a byproduct of a signed distance function applied to tongue meshes representing portions of fissures that are close to each other.

A mesh refinement module (such as curly edges module 512) may refine second initial single-layer mesh 1004 to remove curly edge 1006. The mesh refinement module may use a typical structure of the fissure (e.g., not having curly edges), as well as an understanding of byproducts of algorithms used to generate initial single-layer meshes 1002, 1004 to identify and remove inaccuracies such as curly edge 1006. The mesh refinement module may also use a shape and/or structure of a probability map (e.g., the tongue mesh) from which initial single-layer meshes 1002, 1004 are generated and/or an anatomical structure (e.g., the lung) to remove curly edge 1006. For example, mesh refinement module may compare second initial single-layer mesh 1002 to the probability map to detect portions that do not accurately align with the probability map (e.g., portions that extend beyond the probability map, etc.) and remove such portions.

Figure 11:
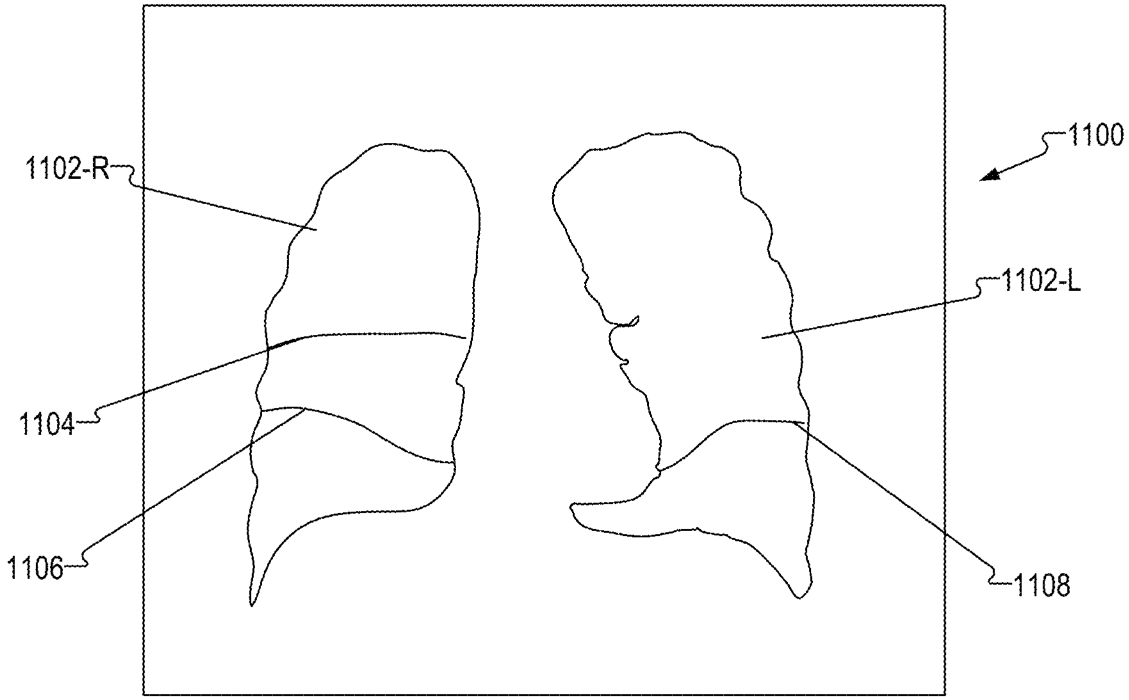
FIGS. 11-13 illustrate exemplary single-layer meshes according to principles described herein.
Figure 12:
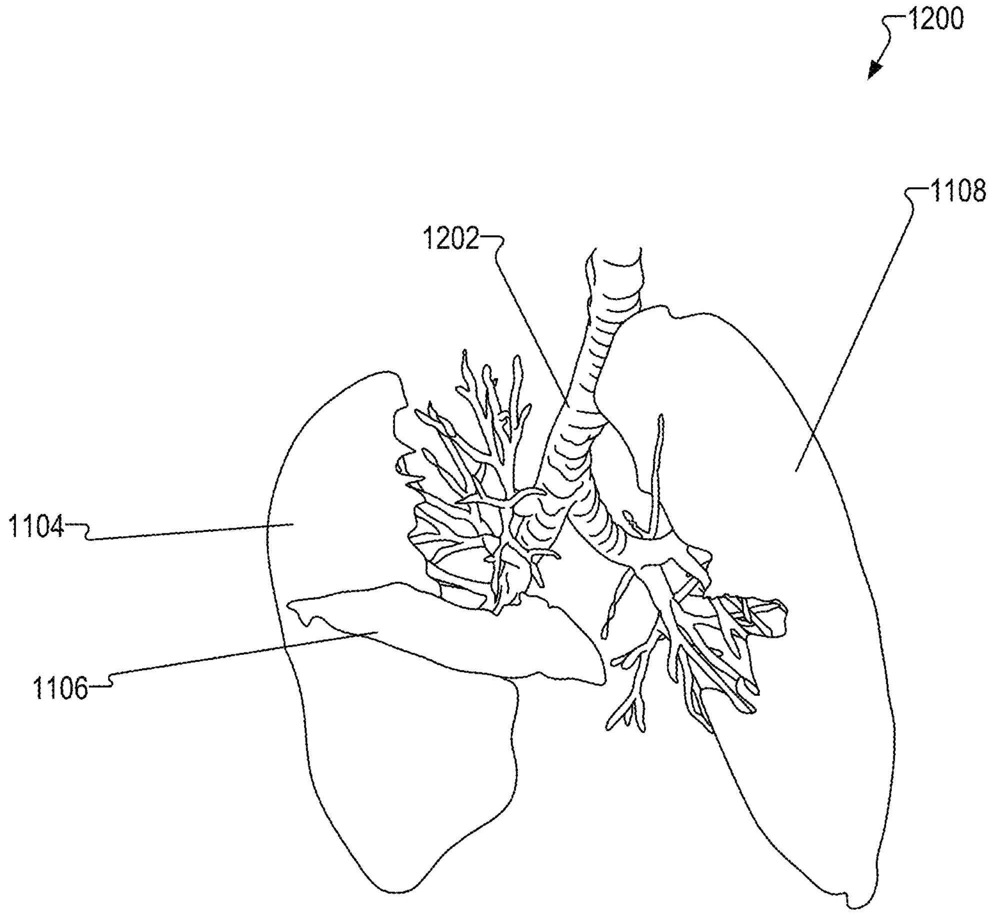

FIGS. 11 and 12 illustrate exemplary single-layer meshes that may be generated by system 100. FIG. 11 shows an image slice 1100 with exemplary single-layer meshes representing fissures in lungs of a patient. Image slice 1100 shows a two-dimensional (2D) slice of a 3D model of a pair of lungs 1102 (shown as right lung 1102-R and left lung 1102-L) of the patient. Image slice 1100 also shows a first single-layer mesh 1104 and a second single-layer mesh 1106 representing two fissures in right lung 1102-R. Image slice 1100 also shows a third single-layer mesh 1108 representing a fissure in left lung 1102-L. Single-layer meshes 1104, 1106, 1108 may be generated by system 100 in any suitable manner, such as by generating an initial single-layer mesh based on a probability map of candidate points and refining the initial single-layer mesh, as described herein.

Comparing image slice 1100 to image slice 600 of FIG. 6, single-layer meshes 1104, 1106, 1108 may provide a more accurate representation of the lung fissures than the tongue meshes provided by probability maps 604, 606, 608. Single-layer meshes 1104, 1106, 1108 may more accurately display actual locations of the fissures, as well as provide a more intuitive representation, as surgeons and surgical team members may expect a single-layer representation of a single-layer anatomical feature such as a fissure.

FIG. 12 shows a perspective view of a 3D visualization 1200 including single-layer meshes, such as first single-layer mesh 1104, second single-layer mesh 1106, and third single-layer mesh 1108. 3D visualization 1200 also shows airway structures 1202 of a patient.

In some examples, 3D visualization 1200 may be an interactive visualization, allowing a user to view different aspects of the patient's lungs and fissures. For example, the user may interact with 3D visualization 1200 to move, rotate, zoom, or otherwise manipulate 3D visualization 1200 to view the lungs, fissures, airways, and other structures and features from different angles and viewpoints. Additionally or alternatively, the user may interact with 3D visualization 1200 to hide, reveal, vary opacity for, etc. different structures and/or features, such as the fissures, the airways, lung structures (e.g., pleura), blood vessels, etc. For example, while FIG. 12 shows single-layer meshes 1104, 1106, and

Figure 13:
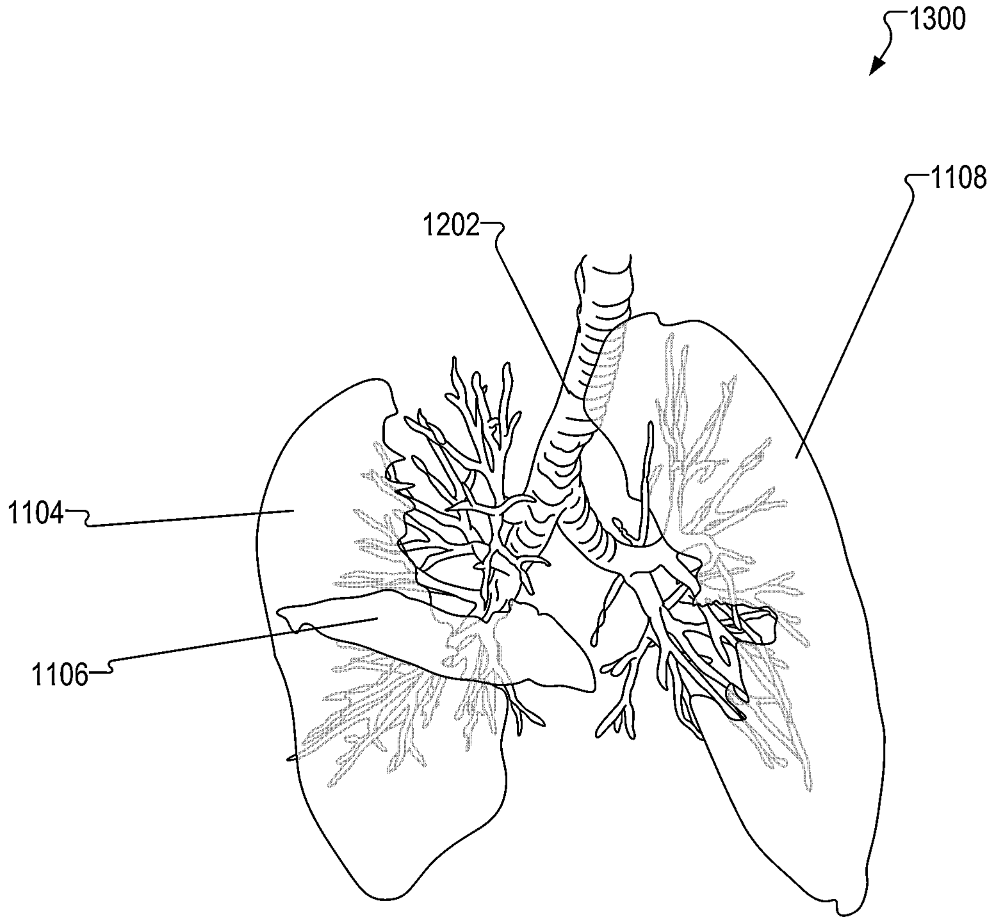

1108 opaquely, such that airway structures 1202 are not visible underneath, 3D visualization 1200 may be manipulated to show single-layer meshes 1104, 1106, 1108 partially or fully translucently, outlined, or in any other suitable manner such that airway structures 1202 may also be visible or only be visible, etc. For example, FIG. 13 shows a 3D visualization 1300 with the same elements, but a more translucent representation of single-layer meshes 1104, 1106, and 1108.

While certain examples described herein are directed to detecting and representing lung fissures, processing system 100 may be configured to detect and represent any suitable single-layer anatomical feature (e.g., a single-layer membrane, ligament, etc.) included in an anatomical structure of a patient.

In some examples, system 100 may also apply a detection process to generate representations of anatomical features such as airway structures 1202. For instance, system 100 may apply a first detection process to detect non-single-layer anatomical features (e.g., airways, blood vessels, etc.) and a second detection process (e.g., different from the first detection process) to detect single-layer anatomical features (e.g., lung fissures). Example second detection processes may include the processes, techniques, and algorithms described above. Example first detection processes are described herein.

Figure 14:
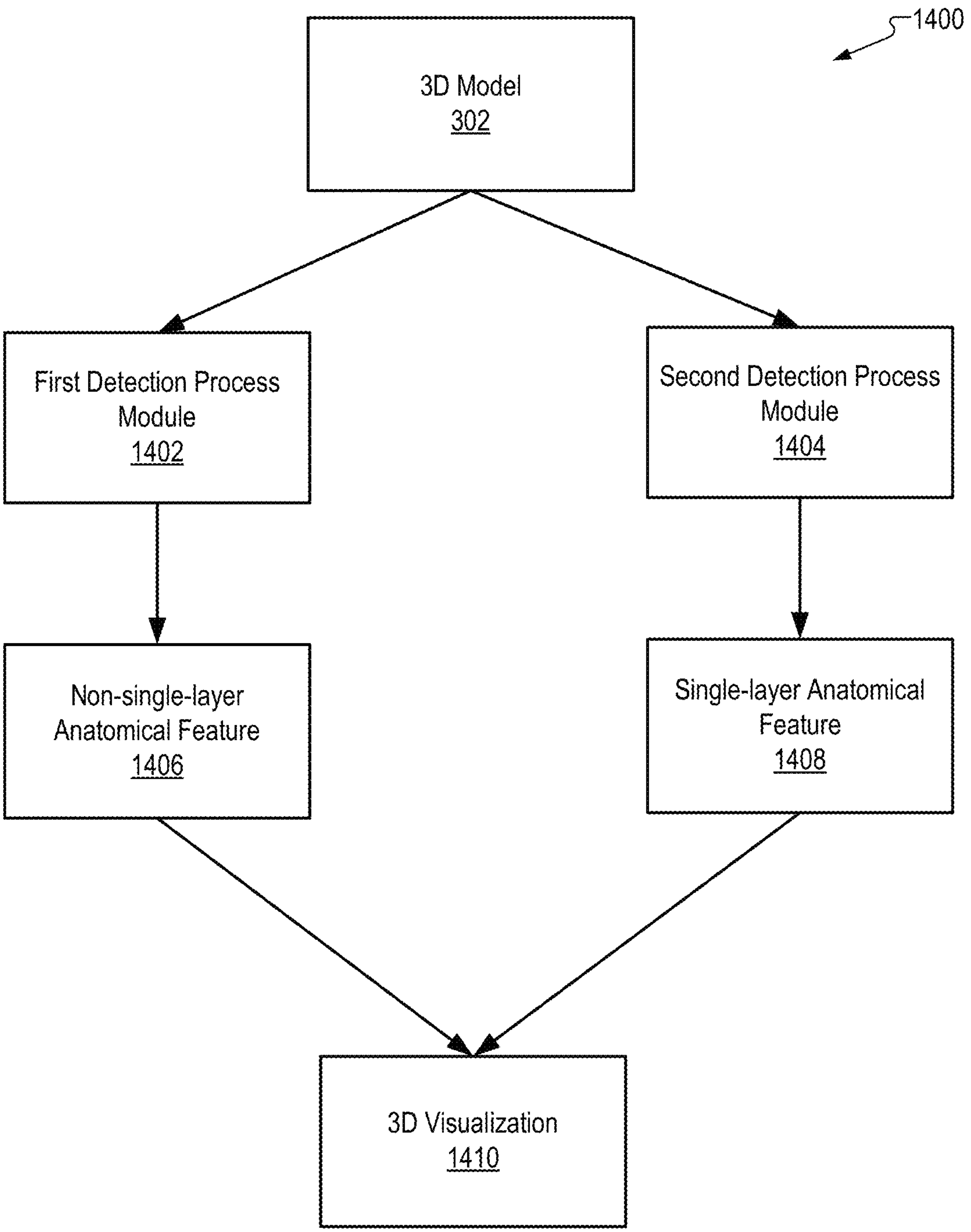
FIGS. 14 and 15 illustrate exemplary configurations for generating a visualization of an anatomical structure using a single-layer mesh according to principles described herein.

FIG. 14 illustrates an exemplary configuration 1400 for generating a visualization of an anatomical structure using a single-layer mesh that may be generated by system 100. Configuration 1400 includes modules that access 3D model 302 of an anatomical structure and generate a 3D visualization 1410 representing the anatomical structure. Configuration 1400 may be implemented by processing system 100 and/or any suitable components of a computer-assisted surgical system, a surgical planning system, or other computer system.

As shown, configuration 1400 includes a first detection process module 1402 and a second detection process module 1404, which access 3D model 302 of the anatomical structure. As described above, 3D model 302 may be generated based on pre-operative images, such as CT scans, MRI scans, X-ray images, etc. First detection process module 1402 may analyze 3D model 302 to detect a first type of anatomical feature such as a non-single-layer anatomical feature 1406. First detection process module 1402 may detect non-single-layer anatomical feature 1406 in any suitable way, such as with a segmentation process applied to 3D model 302 or any other such suitable processes, techniques, and/or algorithms.

Second detection process module 1404 may analyze 3D model 302 to detect a second type of anatomical feature such as a single-layer anatomical feature 1408. Second detection process module 1404 may detect single-layer anatomical feature 1408 using any of the processes, techniques, and/or algorithms described herein.

System 100 may access and use data representative of non-single-layer anatomical feature 1406 and single-layer anatomical feature 1408 to generate 3D visualization 1410 of the anatomical structure, which 3D visualization 1410 may include representations of non-single-layer anatomical feature 1406 and single-layer anatomical feature 1408. For example, 3D visualization 1410 may include 3D visualization 1200 shown in FIG. 12 and that illustrates an exemplary 3D visualization including representations of both non-single-layer anatomical features (e.g., a representation of airway structure 1202) and single-layer anatomical features (e.g., single-layer meshes 1104, 1106, and 1108 representing lung fissures) of an anatomical structure. System 100 may generate 3D visualization 1410 using detected features in any suitable way, such as by using marching cubes or any other suitable volume rendering processes, techniques, and/or algorithms.

Figure 15:
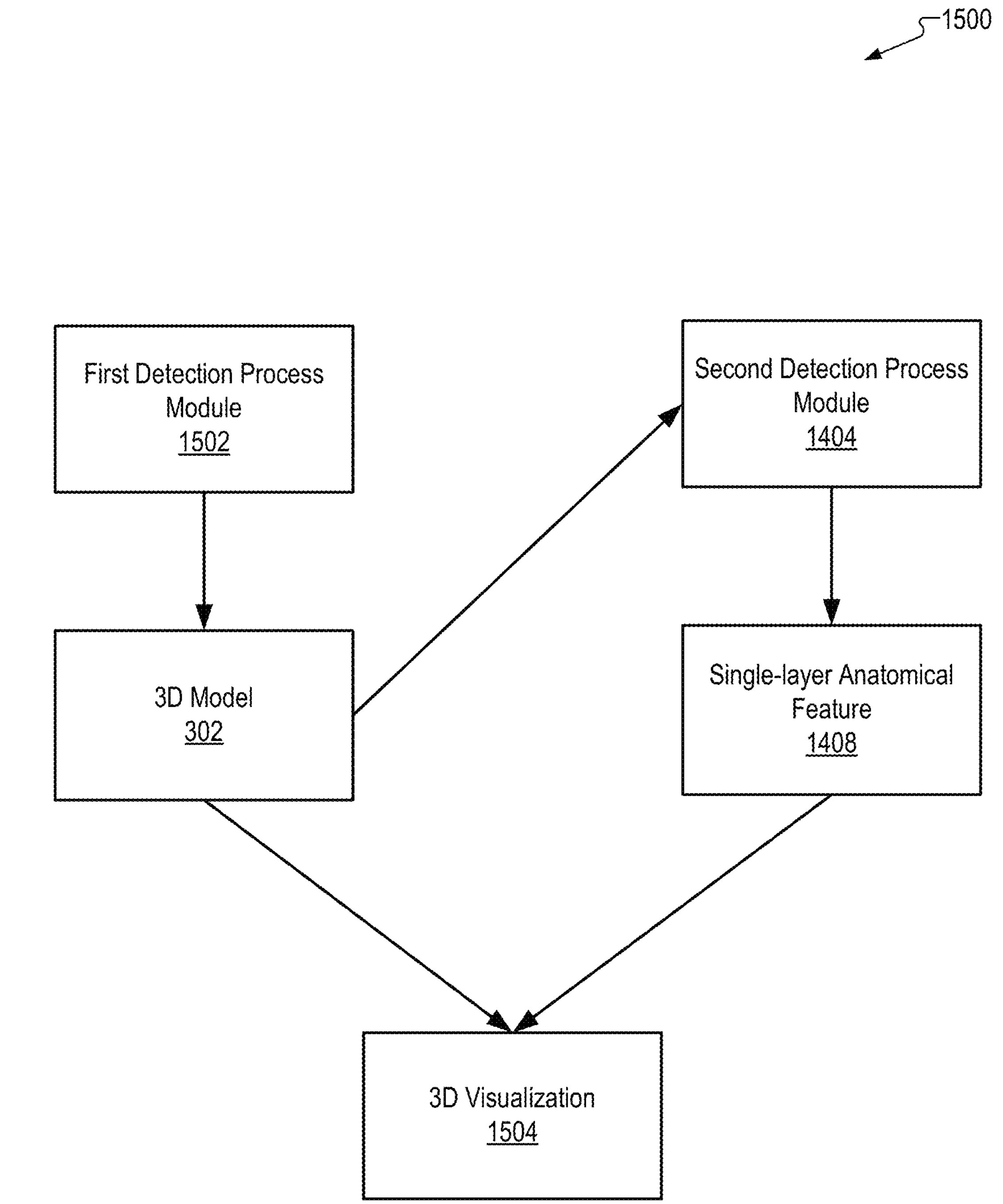

FIG. 15 illustrates an exemplary configuration 1500 for generating a visualization of an anatomical structure using a single-layer mesh that may be generated by system 100. Configuration 1500 includes modules that generate a 3D visualization 1504 representing the anatomical structure. Configuration 1500 may be implemented by processing system 100 and/or any suitable components of a computer-assisted surgical system, a surgical planning system, or other computer system.

As shown, configuration 1500 includes a first detection process module 1502 that generates 3D model 302 of the anatomical structure. As described above, 3D model 302 may be generated based on pre-operative images, such as CT scans, MRI scans, X-ray images, etc. First detection process module 1502 may generate 3D model 302 based on pre-operative images using any suitable techniques and/or algorithms, such as aforementioned segmentation and volume rendering techniques or any other suitable techniques and/or algorithms.

Configuration 1500 also includes second detection process module 1404. As in configuration 1400, second detection process module 1404 may analyze 3D model 302 to detect a single-layer anatomical feature 1408. Second detection process module 1404 may detect single-layer anatomical feature 1408 using any of the processes, techniques, and/or algorithms described herein.

System 100 may access and use data representative of 3D model 302 and single-layer anatomical feature 1408 to generate 3D visualization 1504 of the anatomical structure, which 3D visualization 1504 may include representations of the anatomical structure and single-layer anatomical feature 1408. System 100 may generate 3D visualization 1504 using detected features in any suitable way, such as by using marching cubes or any other suitable volume rendering processes, techniques, and/or algorithms.

In some examples, system 100 may also apply another first detection process on 3D model 302 to additionally detect non-single-layer anatomical features, combining aspects of configuration 1400 and configuration 1500. In other instances, system 100 may apply a first detection process to generate a 3D model, a second detection process to detect single-layer anatomical features, and a third detection process (e.g., different from first and second detection processes) to detect non-single-layer anatomical features.

In some examples, processing system 100 may be implemented by or communicatively connected to one or more components of a surgical system that performs or is used to perform a surgical procedure. A surgical procedure may include any procedure in which manual and/or instrumental techniques are used on a patient to investigate or treat a physical condition of the patient. The surgical system may use information generated by processing system 100, such as a detection and/or a representation of anatomical features in association with a surgical procedure (e.g., for planning, performing, analyzing, and/or other aspects of the surgical procedure). For example, the surgical system may be configured to detect and represent anatomical features of anatomical structures to one or more users of the surgical system. A user of the surgical system may use a representation of a detected anatomical feature for aspects of a surgical procedure. For instance, using the lung fissure example above, the user may use the representation of the detected anatomical feature to plan a potential path to be traversed by a surgical instrument to obtain a biopsy of a nodule of a lung, where the potential path avoids the detected fissures. Additionally or alternatively, the surgical system may be configured to detect anatomical features and use the detection of the anatomical features to determine aspects of the surgical procedure. For instance, using the lung fissure example above, the surgical system may use the detection of the fissures to determine a potential path to be traversed by a surgical instrument to obtain a biopsy of a nodule of a lung, where the potential path avoids the detected fissures.

Data generated by and output by processing system 100 (e.g., data representing a single-layer mesh that represents a single-layer anatomical feature) may be accessed and/or used, in any suitable way, by any appropriately configured computer-assisted surgical system, such as a teleoperated surgical system, a sensor-guided surgical system (e.g., a vision-guided surgical system), etc. For example, data generated by processing system 100 may be used by a computer-assisted surgical system that is configured for minimally invasive surgical procedures. For instance, data generated by processing system 100 may be used by a computer-assisted surgical system in the performance of a bronchoscopic procedure (e.g., a biopsy of a nodule of a lung), such as to plan or facilitate planning of a potential path to be traversed by a surgical instrument (e.g., a teleoperated catheter) to reach a specific location with a lung. Examples of computer-assisted surgical systems that may use data generated by processing system 100 include, without limitation, an ION® system and a DA VINCI® system provided by Intuitive Surgical Operations, Inc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media. Such a non-transitory computer-readable medium storing computer-readable instructions may be implemented by one or more components of a surgical system.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 16:
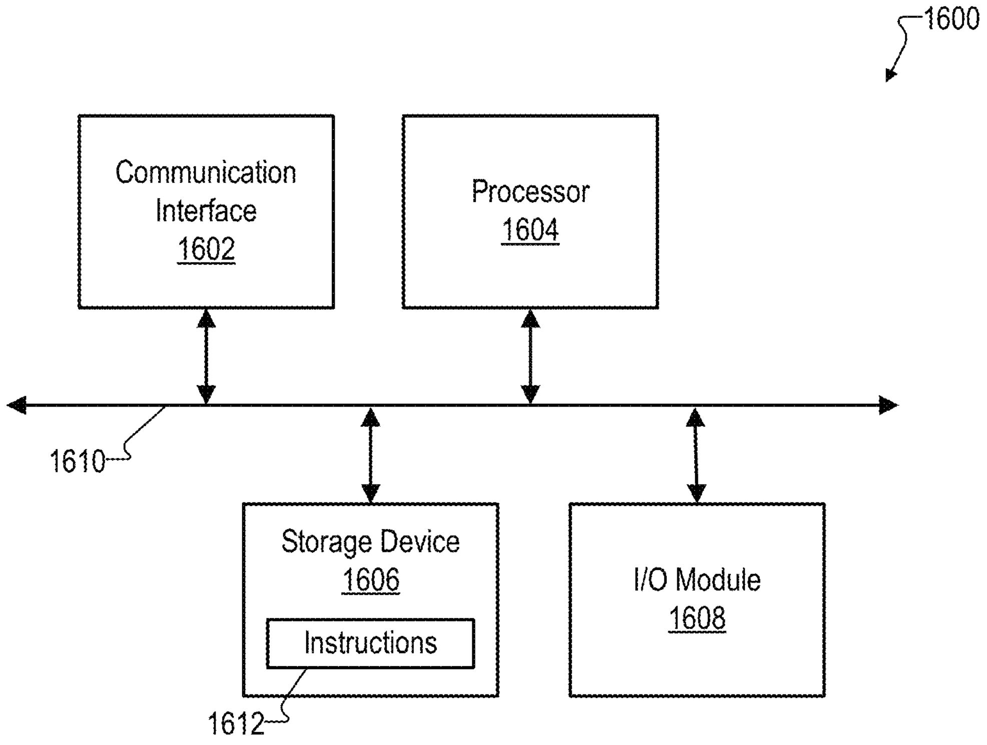
FIG. 16 illustrates an exemplary computing system according to principles described herein.

FIG. 16 illustrates an exemplary computing device 1600 that may be specifically configured to perform one or more of the processes described herein. As shown in FIG. 16, computing device 1600 may include a communication interface 1602, a processor 1604, a storage device 1606, and an input/output ("I/O") module 1608 communicatively connected via a communication infrastructure 1610. While an exemplary computing device 1600 is shown in FIG. 16, the components illustrated in FIG. 16 are not intended to be limiting. Additional or alternative components may be used in other embodiments. Components of computing device 1600 shown in FIG. 16 will now be described in additional detail.

Communication interface 1602 may be configured to communicate with one or more computing devices. Examples of communication interface 1602 include, without limitation, a wired network interface (such as a network interface card), a wireless network interface (such as a wireless network interface card), a modem, an audio/video connection, and any other suitable interface.

Processor 1604 generally represents any type or form of processing unit capable of processing data or interpreting, executing, and/or directing execution of one or more of the instructions, processes, and/or operations described herein. Processor 1604 may direct execution of operations in accordance with computer-executable instructions 1612 (e.g., one or more applications) such as may be stored in storage device 1606 or another computer-readable medium.

Storage device 1606 may include one or more data storage media, devices, or configurations and may employ any type, form, and combination of data storage media and/or device. For example, storage device 1606 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1606. For example, data representative of executable instructions 1612 configured to direct processor 1604 to perform any of the operations described herein may be stored within storage device 1606. In some examples, data may be arranged in one or more databases residing within storage device 1606. In certain implementations, instructions 1612 may include instructions 106 of processing system 100, processor 1604 may include or implement processing facility 104, and storage device 1606 may include or implement storage facility 102.

I/O module 1608 may include one or more I/O modules configured to receive user input and provide user output. One or more I/O modules may be used to receive input for a single virtual reality experience. I/O module 1608 may include any hardware, firmware, software, or combination thereof supportive of input and output capabilities. For example, I/O module 1608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1608 is configured to provide graphical data to a display for presentation to a user. The graphical data may be representative of one or more graphical user interfaces and/or any other graphical content as may serve a particular implementation.

The display may be configured to display a representation of an anatomical structure in any suitable way. The displayed representation of the anatomical structure may represent one or more features of the anatomical structure, such as a single-layer anatomical structure and/or a non-single-layer anatomical structure. The display may be further configured to display, together with the representation of the anatomical structure, a representation of a potential path to be traversed by a surgical instrument in the anatomical structure. The representation of the potential path may depict that the potential path avoids one or more anatomical features of the anatomical structure, such as a single-layer anatomical feature (e.g., by not contacting, intersecting, or coming within a proximity threshold of the single-layer anatomical feature). The representation of the potential path may additionally or alternatively depict that at least part of the potential path is within an anatomical feature of the anatomical structure, such as a non-single-layer anatomical feature.

In certain examples, the display may present a graphical user interface that includes one or more of the visual representations described herein. For example, the graphical user interface may present a representation of an anatomical structure, a representation of a single-layer anatomical feature of the anatomical structure, and/or a non-single-layer anatomical feature of the anatomical structure. The representation of the single-layer anatomical feature may be presented as a feature to be avoided by a potential path to be traversed by a surgical instrument in the anatomical structure. The representation of the non-single-layer anatomical feature may be presented as a feature to be avoided by a potential path to be traversed by a surgical instrument in the anatomical structure or as a potential pathway of at least part of the potential path to be traversed by the surgical instrument in the anatomical structure.

In certain examples, processor 1604 may be configured to receive user input by way of the graphical user interface. The user input may define a potential path to be traversed by the surgical instrument in the anatomical structure. For example, the user input may create and/or modify the potential path to be traversed by the surgical instrument in the anatomical structure. A representation of the defined potential path may be displayed in the graphical user interface and may be helpful for planning a medical procedure to be performed on a patient.

Computing device 1600 may be implemented by or communicatively connected to a computer-assisted surgical system. As an example, computing device 1600 may include or be implemented by a computing system such as a surgical procedure planning computer that may be communicatively coupled to a computer-assisted surgical system. As another example, computing device 1600 may be integrated within a computer-assisted surgical system.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:

a processor configured to:

access a three-dimensional (3D) model of an anatomical structure;

apply a first detection process to the 3D model to detect a single-layer anatomical feature in the anatomical structure, the first detection process comprising generating a single-layer mesh based on a signed distance map including vectors that pass through a set of candidate points for the single-layer anatomical feature;

apply a second detection process, different from the first detection process, to the 3D model to detect a non-single-layer anatomical feature in the anatomical structure; and provide a representation of the anatomical structure based on the 3D model, the detected single-layer anatomical feature, and the detected non-single-layer anatomical feature; and a display communicatively coupled to the processor and configured to display the representation of the anatomical structure and a representation of a potential path to be traversed by a medical instrument in the anatomical structure.

2. The system of claim 1, wherein:

the representation of the anatomical structure represents the detected single-layer anatomical feature; and the potential path avoids the detected single-layer anatomical feature.

3. The system of claim 1, wherein:

the representation of the anatomical structure represents the detected non-single-layer anatomical feature; and at least part of the potential path is within the detected non-single-layer anatomical feature.

4. The system of claim 1, wherein:

the single-layer anatomical feature comprises a lung fissure; and the non-single-layer anatomical feature comprises an airway.

5. The system of claim 1, wherein the representation of the potential path to be traversed by the medical instrument in the anatomical structure represents a path to be traversed by the medical instrument to obtain a biopsy of a nodule of a lung.

6. The system of claim 1, wherein the processor is configured to generate, based on the 3D model, the detected single-layer anatomical feature, and the detected non-single-layer anatomical feature, the representation of the potential path to be traversed by the medical instrument in the anatomical structure, the potential path avoiding the detected single-layer anatomical feature.

7. The system of claim 1, wherein:

the display is configured to display the representation of the anatomical structure in a graphical user interface; and the processor is configured to receive, by way of the graphical user interface, user input defining the potential path to be traversed by the medical instrument in the anatomical structure.

8. The system of claim 7, wherein the graphical user interface presents one or more of:

a representation of the single-layer anatomical feature to be avoided by the potential path to be traversed by the medical instrument in the anatomical structure; or a representation of the non-single-layer anatomical feature as a potential pathway of at least part of the potential path to be traversed by the medical instrument in the anatomical structure.

9. A non-transitory computer-readable medium storing instructions executable by a processor to:

access a three-dimensional (3D) model of an anatomical structure;

apply a first detection process to the 3D model to detect a single-layer anatomical feature in the anatomical structure, the first detection process comprising generating a single-layer mesh based on a signed distance map including vectors that pass through a set of candidate points for the single-layer anatomical feature;

apply a second detection process, different from the first detection process, to the 3D model to detect a non-single-layer anatomical feature in the anatomical structure;

generate a representation of the anatomical structure based on the 3D model, the detected single-layer anatomical feature, and the detected non-single-layer anatomical feature;

generate a representation of a path to be traversed by a medical instrument in the anatomical structure; and provide, to a display communicatively coupled to the processor, the representation of the anatomical structure and the representation of the path to be traversed by the medical instrument in the anatomical structure.

10. The non-transitory computer-readable medium of claim 9, wherein:

the representation of the anatomical structure represents the detected single-layer anatomical feature; and the path avoids the detected single-layer anatomical feature.

11. The non-transitory computer-readable medium of claim 9, wherein:

the representation of the anatomical structure represents the detected non-single-layer anatomical feature; and at least part of the path is within the detected non-single-layer anatomical feature.

12. The non-transitory computer-readable medium of claim 9, wherein:

the single-layer anatomical feature comprises a lung fissure; and the non-single-layer anatomical feature comprises an airway.

13. The non-transitory computer-readable medium of claim 9, wherein the representation of the path to be traversed by the medical instrument in the anatomical structure represents a pathway to be traversed by the medical instrument to obtain a biopsy of a nodule of a lung.

14. The non-transitory computer-readable medium of claim 9, wherein the instructions are further executable by the processor to generate the representation of the path to be traversed by the medical instrument in the anatomical structure based on the 3D model, the detected single-layer anatomical feature, and the detected non-single-layer anatomical feature, the path avoiding the detected single-layer anatomical feature.

15. The non-transitory computer-readable medium of claim 9, wherein the instructions are further executable by the processor to generate the representation of the path to be traversed by the medical instrument in the anatomical structure based on user input defining the path to be traversed by the medical instrument in the anatomical structure.

16. The non-transitory computer-readable medium of claim 15, wherein the user input is received by way of a graphical user interface presenting at least one of:

a representation of the single-layer anatomical feature to be avoided by the path to be traversed by the medical instrument in the anatomical structure; or a representation of the non-single-layer anatomical feature as a potential pathway of at least part of the path to be traversed by the medical instrument in the anatomical structure.

17. A method performed by a computer processor, the method comprising:

accessing a three-dimensional (3D) model of an anatomical structure;

applying a first detection process to the 3D model to detect a single-layer anatomical feature in the anatomical structure, the first detection process comprising generating a single-layer mesh based on a signed distance map including vectors that pass through a set of candidate points for the single-layer anatomical feature;

applying a second detection process, different from the first detection process, to the 3D model to detect a non-single-layer anatomical feature in the anatomical structure;

generating a representation of the anatomical structure based on the 3D model, the detected single-layer anatomical feature, and the detected non-single-layer anatomical feature;

generating a representation of a path to be traversed by a medical instrument in the anatomical structure; and providing, to a display communicatively coupled to the computer processor, the representation of the anatomical structure and the representation of the path to be traversed by the medical instrument in the anatomical structure.

18. The method of claim 17, further comprising:

providing, to a computer-assisted surgical system, data representative of at least one of the 3D model, the detected single-layer anatomical feature, the detected non-single-layer anatomical feature, or the path to be traversed by the medical instrument in the anatomical structure.

19. The method of claim 17, wherein the medical instrument comprises a teleoperated catheter.

20. The method of claim 17, wherein:

the representation of the anatomical structure represents the detected single-layer anatomical feature and the detected non-single-layer anatomical feature;

the path avoids the detected single-layer anatomical feature; and at least part of the path is within the detected non-single-layer anatomical feature.

* * * * *